United States Patent
Lyon

(10) Patent No.: US 10,184,908 B2
(45) Date of Patent: Jan. 22, 2019

(54) METAL DETECTION APPARATUS

(71) Applicant: Mettler-Toledo Safeline Ltd., Manchester (GB)

(72) Inventor: David Lyon, Cheadle (GB)

(73) Assignee: Mettler-Toledo Safeline Ltd., Manchester (GB)

( * ) Notice: Subject to any disclaimer, the term of this patent is extended or adjusted under 35 U.S.C. 154(b) by 210 days.

(21) Appl. No.: 15/379,816

(22) Filed: Dec. 15, 2016

(65) Prior Publication Data
US 2017/0176364 A1     Jun. 22, 2017

(30) Foreign Application Priority Data
Dec. 17, 2015   (EP) .................................... 15200784

(51) Int. Cl.
| | |
|---|---|
| *G01N 27/02* | (2006.01) |
| *G01V 3/10* | (2006.01) |
| *H03F 1/02* | (2006.01) |
| *H03F 3/195* | (2006.01) |
| *H03F 3/24* | (2006.01) |

(52) U.S. Cl.
CPC ........... *G01N 27/023* (2013.01); *G01V 3/105* (2013.01); *H03F 1/0205* (2013.01); *H03F 3/195* (2013.01); *H03F 3/245* (2013.01); *H03F 2200/451* (2013.01); *H03F 2200/541* (2013.01)

(58) Field of Classification Search
CPC ..... G01N 27/023; H03F 3/245; H03F 1/0205; H03F 3/195; H03F 2200/541; H03F 2200/451; G01V 3/105

USPC .......................................... 324/654, 649, 600
See application file for complete search history.

(56) References Cited

U.S. PATENT DOCUMENTS

| | | |
|---|---|---|
| 4,609,879 A | 9/1986 | Flachenecker et al. |
| 8,841,903 B2 | 9/2014 | Lyon |
| 9,910,053 B2 * | 3/2018 | Bakhru .............. G01N 33/4905 |
| 2003/0107377 A1 | 6/2003 | Uzman |

(Continued)

*Primary Examiner* — Giovanni Astacio-Oquendo
(74) *Attorney, Agent, or Firm* — Standley Law Group LLP

(57) ABSTRACT

A metal detector has a transformer unit (1), a transmitter unit (2), a receiver coil set (3), a signal processing unit (4) and a control unit (5). The transformer unit provides an input signal ($s_{IN}$) with selectable operating frequency ($f_{TX}$) to an amplifier stage (12), that is connected to a transmitter coil (21) that is coupled to first and second receiver coils (31, 32). The coil outputs are connected to the signal processing unit, which has a receiver unit (41) and a signal processor (42). A coupling transformer (13) has first and second windings (13A, 13B), connected to the output of the amplifier stage, and a third winding (13C), connected to the transmitter coil. The first and second windings are each connected at a first end to a supply voltage (+Ub). Each of the first and second windings has at least one tapping (141, 142, 143, 144; 141', 142', 143', 144') at a same turn number counted from the first end. The amplifier stage has first and second amplification wings (12A, 12B). Each of these is associated with a power transistor connected to one of the at least one tappings of the corresponding winding, so the first and second amplification wings amplify the corresponding first and second half waves of the input signal.

18 Claims, 2 Drawing Sheets

(56) References Cited

U.S. PATENT DOCUMENTS

| | | | |
|---|---|---|---|
| 2014/0320144 A1* | 10/2014 | Nakaya | H01M 10/54 324/434 |
| 2016/0054265 A1* | 2/2016 | Zhong | H03K 17/102 250/290 |
| 2017/0165592 A1* | 6/2017 | Hunter | B01D 19/0031 |
| 2017/0264110 A1* | 9/2017 | Toya | H02J 7/0021 |
| 2018/0088018 A1* | 3/2018 | Inoue | G01N 15/0656 |

\* cited by examiner

METAL DETECTION APPARATUS

CROSS-REFERENCE TO RELATED APPLICATIONS

This application claims priority under 35 USC 119 to European patent application EP 15 200 784.5, filed on 17 Dec. 2015, the content of which is incorporated by reference as if fully recited herein.

TECHNICAL FIELD

The invention relates to a metal detection apparatus that uses one or more operating frequencies.

BACKGROUND

A metal detection apparatus is used to detect metal contamination in edible goods and other products. Modern metal apparatuses utilise a search head that comprises a "balanced coil system" typically with three coils that are wound onto a non-metallic frame. A transmitter coil located in the centre is energised with a high frequency electric current that generates a magnetic field. Two coils on each side of the transmitter coil act as receiver coils. Since the two receiver coils are identical and installed with the same distance from the transmitter coil, an identical voltage is induced in each of them. In order to receive an output signal that is zero when the system is in balance, the first receiver coil is connected in series with the second receiver coil having an inversed sense of winding. Hence the voltages induced in the receiver coils, that are of identical amplitude and inverse polarity are cancelling out one another in the event that the system, in the absence of metal contamination, is in balance.

As a particle of metal passes through the coil arrangement, the high frequency field is disturbed first near one receiver coil and then near the other receiver coil. While the particle of metal is conveyed through the receiver coils the voltage induced in each receiver coil is changed typically in the range of nano-volts. This change in balance results in a signal at the output of the receiver coils that can be processed, amplified and subsequently be used to detect the presence of the metal contamination in a product.

The signal processing channels normally split the received signal into two separate components that are 90° apart from one another. The resultant vector has a magnitude and a phase angle, which is typical for the products and the contaminants that are conveyed through the coils. In order to identify a metal contaminant, "product effects" need to be removed or reduced. If the phase of the product is known, then the corresponding signal vector can be reduced. Eliminating unwanted signals from the signal spectrum thus leads to higher sensitivity for signals originating from contaminants.

Methods applied for eliminating unwanted signals from the signal spectrum therefore exploit the fact that the contaminants, the product and other disturbances have different influences on the magnetic field so that the resulting signals differ in phase.

Distinguishing between the phases of the signal components of different origin by means of a phase detector allows obtaining information about the product and the contaminants. A phase detector, e.g. a frequency mixer or analogue multiplier circuit, generates a voltage signal which represents the difference in phase between the signal input, such as the signal from the receiver coils, and a reference signal provided by the transmitter unit to the receiver unit. Hence, by selecting the phase of the reference signal to coincide with the phase of the product signal component, a phase difference and a corresponding product signal is obtained at the output of the phase detector that is zero. In the event that the phase of the signal components that originate from the contaminants differ from the phase of the product signal component, then the signal components of the contaminants can be detected. However, if the phase of the signal components of the contaminants is close to the phase of the product signal component, then the detection of contaminants fails, since the signal components of the contaminants are suppressed together with the product signal component. In known systems, the transmitter frequency is therefore selectable in such a way that the phase of the signal components of the metal contaminants will be out of phase with the product signal component.

U.S. Pat. No. 8,841,903 B2 discloses the metal detection apparatus shown below in FIG. 1, which comprises a transmitter unit 2 that provides transmitter signals to a transmitter coil 21 that is inductively coupled to first and second receiver coils 3, 31, 32, which are connected to the input of a signal processing unit 4 that comprises a receiver unit 41 connected to a signal processor 42. The transformer unit 1 comprises a frequency generator 11 that provides an operating frequency $f_{TX}$ to the input of an amplifier stage 12, whose output is connected via a coupling transformer 13 to the transmitter coil 21 in transmitter unit 2. The output of the amplifier stage 12 is connected via a first switch bank 14 to a first tapping 141; 142; 143 and the transmitter coil 21 is connected via a second switch bank to a second tapping 151; 152; 153; 154 of the same transformer winding 131 of the transformer 13. The transformer winding 131 has a number of n winding coils between the first tapping 141; 142; 143 and a common potential and a number of n+m winding coils between the second tapping 151; 152; 153; 154 and the common potential. The transmitter coil 21 comprises a number of q winding coils and is connected via a third switch bank 23 to tuning capacitors 221, 222, 223 or combinations thereof thus forming a resonant circuit that is tuned to the operating frequency $f_{TX}$. The ratio n+m/q of the winding coils of the transformer winding 131 and the winding coils of the transmitter coil 21 is selected such that the inductance of the transformer winding 131 is at least ten times higher than the inductance of the transmitter coil 21.

With this arrangement, the resonant circuit, which consists of the transmitter coil 21 and the selectable capacitors 221, 222, 223, can be tuned optimally and independently of other parts of the transmitter unit. Due to the difference in inductances, the transformer 13 is decoupled from the resonant circuit allowing individual optimization of the different parts of the transmitter.

The amplifier stage consists of a class A or B amplifier that can be selected to provide an output signal in a suitable voltage range, e.g. 20 Vpp.

For phase detection of the response signals the transformer 13 comprises a further transformer winding 132 having a first and a second tapping 1321, 1323 and a centre tapping 1322 arranged therebetween. The voltage appearing across the second winding 132, which is fed as a reference signal $s_{REF}$ to the signal processor 42, corresponds exactly to the signal appearing across the receiver coil 3 when no products P and/or contaminants C pass through the balanced coil system 21, 3. Hence, with the reference signal $s_{REF}$ changes of the received signal induced by products P or contaminants C can exactly be detected. Since the reference signal $s_{REF}$ is phase-locked to the transmitter signal $s_{TX}$ at the output of the power amplifier 12 changes in the response signal can accurately be detected.

FIG. 1 further symbolically shows a conveyor 8, on which products P, which may comprise contaminants C, are transferred through the transmitter coil 21 and the receiver coils 31, 32.

This advantageous circuit arrangement still has drawbacks. A Class A circuit amplifies signals with minimum distortion, but with low efficiency since the power transistor consumes current continuously even in the quiescent state. Amplifier efficiency is defined as the ratio of AC power input to the load divided by the DC power consumed by the circuit. When at or near maximum output power, the efficiency of a typical Class A amplifier is only 40%, about 10% less than its theoretical 50% maximum. With reduced output power, the efficiency drops accordingly.

Class AB circuitry avoids crossover distortion to a large extent and operates with reduced losses, since in the quiescent state, due to the applied biases to the complementary pair of transistors, only a small collector current is present. This circuit requires complementary amplification wings typically with a PNP and a NPN power transistor arranged as emitter followers. Providing different but complementary amplification wings requires different electronic elements and a different design for each amplifier wing and therefore considerable manufacturing efforts. Furthermore, Class AB amplifier stages, with a "push-pull" circuit typically deliver at the emitters of the complementary power transistors an output voltage that is applied to the load. In order to avoid a drop in voltage, which is not compensated for, the output voltage is applied directly to the load thus avoiding connecting cables.

Further, the Class AB circuitry does not deliver reference signals for phase detection, wherefore said additional winding 132 is required in the transformer 13 with the result of additional manufacturing costs.

Furthermore, the options to tune and adapt the resonant circuit, consisting of the transmitter coil and the tuning capacitors, to the frequency of the input signal are limited. Hence, the metal detection apparatus operates with a limited range of operating frequencies. It is an object to provide an improved metal detection apparatus that overcomes this limitation.

SUMMARY

The above and other objects of the present invention are achieved by a metal detection apparatus as defined in the appended claims.

The metal detection apparatus comprises a transmitter unit with a frequency generator that provides an input signal with a selectable operating frequency to the input of an amplifier stage, whose output is connected via a coupling transformer to a transmitter coil that is coupled to a first and a second receiver coil, which are connected to a signal processing unit that includes a receiver unit connected to a signal processor.

According to the invention the coupling transformer comprises a first winding and a second winding that are connected to the output of the amplifier stage and a third winding that is connected to the transmitter coil. The first and second windings are connected with a first end to a supply voltage and have each at least one tapping at a same turn number counted from said first end. The amplifier stage comprises a first amplification wing with at least a first power transistor connected to the at least one tapping of the first winding and a second amplification wing with at least a second power transistor connected to the at least one tapping of the second winding and wherein the first amplification wing amplifies the first half wave and the second amplification wing amplifies the second half wave of the input signal.

The transmitter unit of the inventive metal detection apparatus, including the amplifier stage and the coupling transformer, comprises an almost symmetrical structure, which yields several advantages.

The amplifier stage can be set up with two wings, which operate identically and which can deliver drive signals with high efficiency and low distortions to almost identical loads in the form of the first and second winding. Due to the symmetry, identical electronic elements, such as transistors and resistors, can be selected at lower cost having improved specifications. Distortions occurring in the amplifier stage are comparable to the ones occurring in a Class A amplifier, while the efficiency is at least in the range of a Class AB amplifier.

The first and second windings of the coupling transformer preferably comprise identical numbers of turns with the respective first and second tappings connected to identical turn numbers of the first and the second winding. Hence, in an optimal embodiment the first and second windings of the coupling transformer exhibit complete symmetry.

The first and the second power transistor are connectable via a related first or second switch to a respective first or second tapping. The first and second switch are controlled by a control unit such that the power transistors are always connected to corresponding tappings so that full symmetry is maintained.

In a preferred embodiment, the amplifier wings are designed such that the collectors of the first and the second power transistor are connectable via the first or second switch to the respective first or second tapping of the coupling transformer therefore to identical loads. The first end of the first winding and first end of the second winding are connected to a first supply voltage. The first winding and the second winding preferably have an inverse sense of winding relative to one another. This allows using identical high-power stages with identical power transistors which amplify half waves of the input signal having the same polarity. For this purpose, a half wave of the input signal is applied inverted to the amplifier stage or is inverted within the amplifier stage and then is inverted again by the coupling transformer due to the inverse sense of winding of the first or second winding in order to apply a full wave signal to the transmitter coil 21.

Using identical power transistors, particularly identical NPN-power transistors, provides considerable advantages. In Tietze/Schenk, Halbleiterschaltungstechnik, 11$^{th}$ Edition, Heidelberg 1999, Chapter 4.1, page 301-307, it is stated that properties of PNP and NPN transistors differ with PNP transistors being inferior. Further it is stated that in bipolar-technology NPN- and PNP-Transistors are manufactured in separate processes. Consequently, conventional Class B or Class AB amplifiers with complementary power stages exhibit undesirable non-linearities if the transistors are not carefully selected and matched.

This problem is avoided with the inventive amplifier stage in which complementary amplifier wings operate with identical transistors, preferably NPN-transistors, and identical circuits, in which the power transistors are embedded. Tietze/Schenk state that a manufacturing tolerance in a process step influences all NPN-transistors in the same manner. Hence, preferably NPN-transistors of the same manufacturing cycle are selected, which is a simple administrative task. Furthermore, the additional elements of the power stage, particularly the emitter resistors, can easily be selected so that complete symmetry can be reached and distortions are avoided.

The power transistors, in the embodiment of a conventional transistor or MOSFET, are preferably implemented as a voltage follower or current source with variable input voltage. The collector of each power transistor is connected to the load, i.e. the respective first or second winding of the coupling transformer which are connected to a supply voltage. Both power transistors act in such a way that the voltage across the emitter resistors, which act as current sensing resistors, follow the input voltage. Consequently, the current through the respective first or second winding follows the input signal. If the input voltage varies, this arrangement will act as a voltage-to-current converter (voltage-controlled current source VCCS).

In a preferred embodiment, the centre tapping of the primary windings of the coupling transformer, i.e. the first ends of the first and second windings of the coupling transformer, is or are connected to a first supply voltage and the emitter resistors are connected to a second supply voltage with opposite voltage potential. Consequently, the voltage difference between the first and the second supply voltage can be applied individually to each amplifier wing. In the event that the power supply delivers +15 V and −15 V to the power amplifier, then 30 V can be applied to each amplifier wing for the amplification of one half wave each, while in a conventional Class-A, Class-B or Class-AB amplifier these voltages would be used for the amplification of both half waves. Hence, the inventive metal detection apparatus operates with doubled efficiency.

The inventive use of voltage-controlled current sources with doubled efficiency allows conducting the collector currents to the coupling transformer via cables over longer distances without impairment. Changes of the load due to the use of a connecting cable will not change the current, since the current follows the input signal and not the load. Consequently the inventive transmitter stage allows a modular set up of the metal detection system. A first housing can be provided for transmitter stage, which can be connected via cables to one or more detector heads that include a coupling transformer.

Still further, the electronic circuit with the embedded power transistor uses a biasing which allows amplifying high input signals.

Furthermore, the signals at the collectors of the first and the second power transistor that are forwarded to the selected first and second tappings can advantageously be used as high precision reference signals in the signal processing unit. An additional winding on the coupling transformer is thus avoided.

The power transistors are driven by amplification units, preferably operational amplifiers. A phase change by 180° in one of the amplifier wings can advantageously be reached by applying the input signal in the first amplifier wing to an inverting input of the operational amplifier and in the second amplifier wing to a noninverting input of the operational amplifier.

In a preferred embodiment first and second windings are primary windings of the coupling transformer and the third winding is a secondary winding of the coupling transformer. The third winding of the coupling transformer preferably comprises a plurality of tappings. A first end of the transmitter coil is connected to one of these tappings and the second end of the transmitter coil is selectively connectable via a third switch to one of the other tappings. With this arrangement of the coupling transformer having two primary windings connected to the amplifier stage and one secondary winding connected to the transmitter coil the transmitter coil can be adapted in a wider range to the amplifier stage. The ratio of the inductance of the first and second windings of the transformer and the inductance of the transmitter coil is selectable for example in the range of 50:1 up to 2000:1.

Furthermore, together with tuning capacitors the transmitter coil forms a resonant circuit that can optimally be tuned. The first end of the transmitter coil is selectively connectable via a third switch to one side of one of the tuning capacitors and the second end of the transmitter coil is connected directly or via a plurality of turns of the third winding to the other side of the tuning capacitors. By connecting at least one of the tuning capacitors via a number of turns of the third winding of the coupling transformer to the transmitter coil the resulting resonant circuit can be tuned to far lower frequencies. Consequently the metal detection apparatus can operate with a broader range of operating frequencies.

BRIEF DESCRIPTION OF THE DRAWINGS

Some of the objects and advantages of the present invention have been stated, others will appear when the following description is considered together with the accompanying drawings, in which.

DETAILED DESCRIPTION

Figure 1:
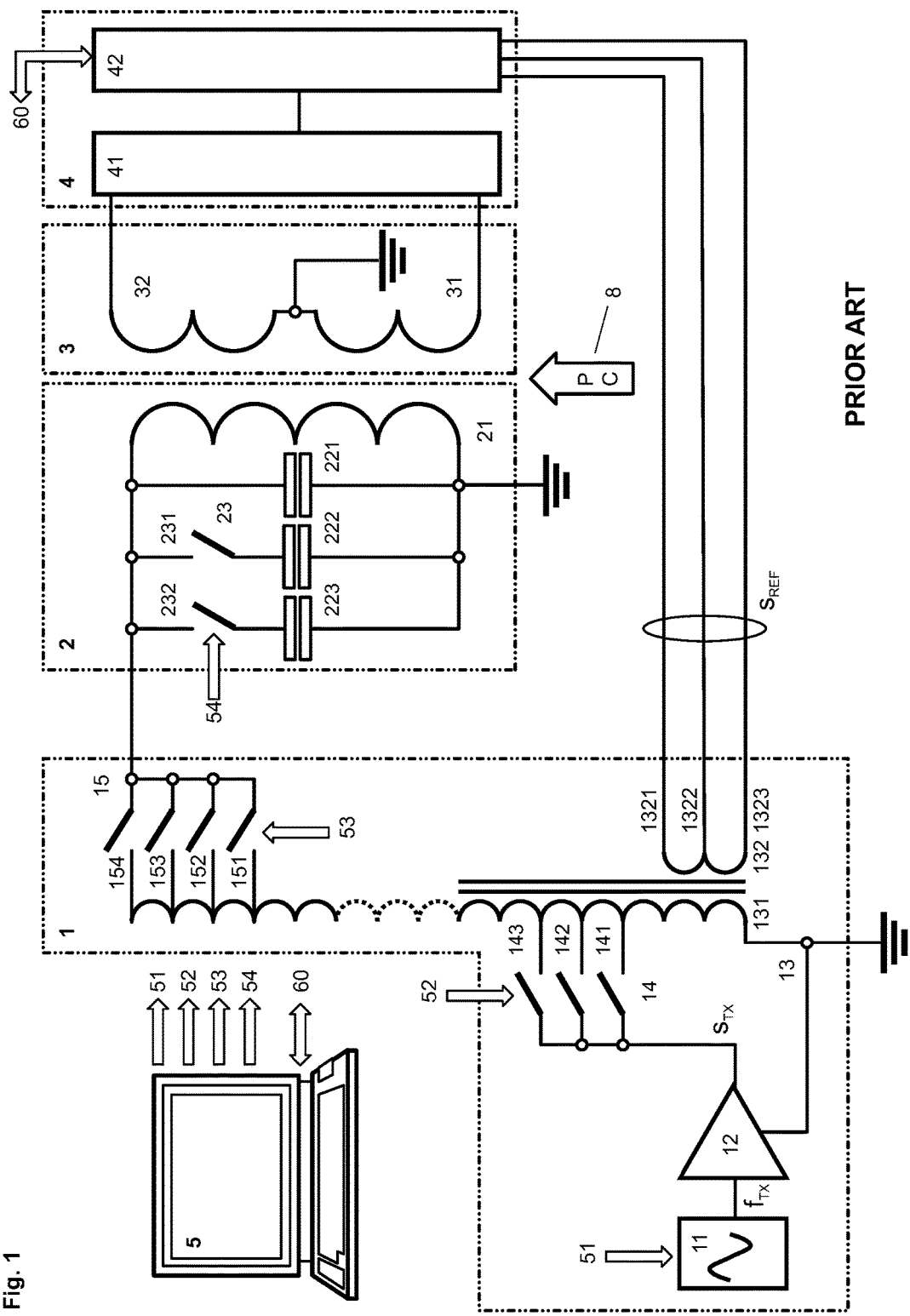
FIG. 1 shows a block diagram of the metal detection apparatus disclosed in U.S. Pat. No. 8,841,903 B2.

FIG. 1 shows a block diagram of the metal detection apparatus disclosed in U.S. Pat. No. 8,841,903 B2, which has been described above. The present invention is an improvement of this apparatus but can also be applied without limitation in other systems.

Figure 2:
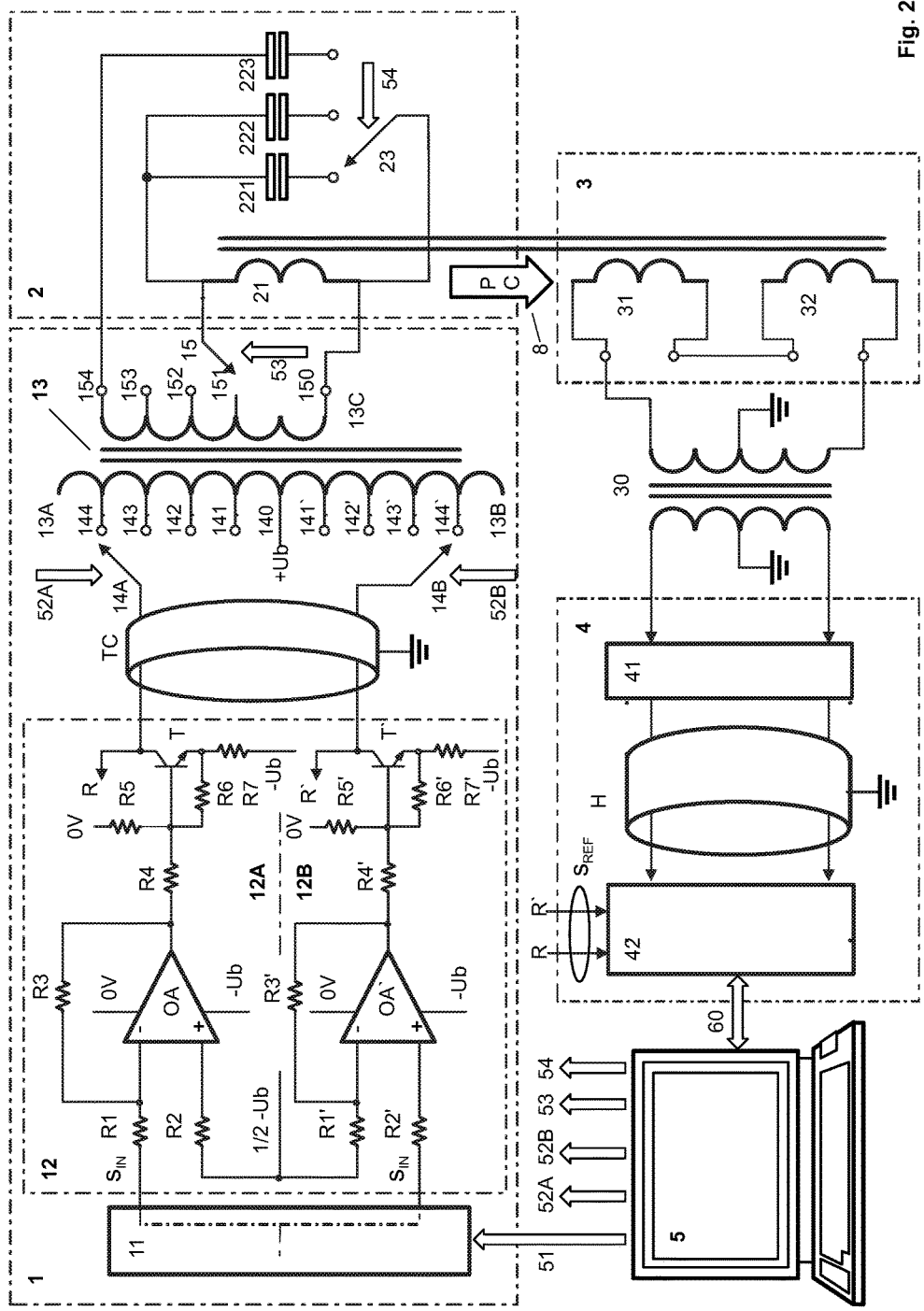
FIG. 2 shows a block diagram of the inventive metal detection apparatus.

FIG. 2 shows a block diagram of a preferred embodiment of the inventive metal detection apparatus, which comprises a transformer unit 1, a balanced coil system with a transmitter coil 21 in a transmitter unit 2, a first and a second receiver coil 31, 32, a signal processing unit 4 with a receiver unit 41 and a signal processor 42, and a control unit 5 that comprises standard interfaces, input devices and output devices, preferably a keyboard and a monitor. FIG. 2 further symbolically shows a conveyor 8, on which products P, which may comprise contaminants C, are transferred through the transmitter coil 21 and the receiver coils 31, 32.

The transformer unit 1 comprises a frequency generator 11 that provides an input signal $s_{IN}$ with a selectable operating frequency $f_{TX}$ to an upper and a lower amplifier wing 12A, 12B provided in the amplifier stage 12. Each amplifier wing 12A, 12B comprises a preamplifier in the embodiment of a first or second operational amplifier OA, OA' respectively, which amplifies a half wave of the input signal $s_{IN}$ that is applied via resistor R1 to the inverting input of the first operational amplifier OA and via resistor R2' to the noninverting input of the second operational amplifier OA'. The noninverting input of the first operational amplifier OA and the inverting input of the second operational amplifier OA' are connected via resistor R2 and resistor R1' to one another and to a voltage potential corresponding to half of a first supply voltage −Ub. The outputs of the first and second operational amplifiers OA, OA' are connected via resistors R3, R3' to their inverting input and via resistors R4, R4' to the base of a respective first or second power transistor T, T'.

Since input signal $s_{IN}$ is applied to the inverting input of the first operational amplifier OA the positive half wave of the input signal $s_{IN}$ is inversed and is then amplified in the first amplifier wing 12A. I.e., both, the first and the second operational amplifier OA and OA' deliver negative half waves to the base of the respective first or second power transistor T, T', which are connected via resistors R5, R5' to zero potential 0V and via resistors R6, R6' to their emitter, which is connected via resistor R7 or R7', respectively, to the first supply voltage −Ub. The collector of the first power transistor T is connected via a first switch 14A to one of a plurality of tappings 141, 142, 143, 144 of the first winding 13A of the coupling transformer 13. The collector of the second power transistor T' is connected via a second switch 14B to one of a plurality of tappings 141', 142', 143', 144' of the second winding 13B of the coupling transformer 13. The first and second winding 13A, 13B, which are designed identically but coiled inversely, are connected with a first end to one another at a common tapping 140 and to a second supply voltage +Ub. The tappings 141, 142, 143, 144 and 141', 142', 143', 144' are located at the same turn numbers counted from said common tapping 140. The first and second switches or switch banks 14A, 14B are controlled such that always tappings 141, 141'; 142, 142'; 143, 143'; 144, 144' are selected that correspond to one another so that identical loads are applied to the power transistors T, T' and symmetry is maintained. With the current settings of switches 14A and 14B, the coil windings between tapping 140 and 144 form the load for the first power transistor T and the coil windings between tapping 140 and 144' form the load for the second power transistor T', which both are connected to the second supply voltage +Ub.

Hence, in this preferred embodiment the power stages with the power transistors T, T' in the amplifier wings 12A, 12B are fully identical. Identical NPN-power transistors and high precision emitter resistors R7, R7' can be selected from the same production series. Consequently, full symmetry in the amplifier wings 12A, 12B is obtained and maintained with each setting of the switches 14A, 14B.

Since the second supply voltage +Ub is applied via the load, the tapped windings 13A or 13B, to the collector and the first supply voltage −Ub is applied via the emitter resistors R7 or R7' to the emitter of the first or second power transistor T, T', the voltage difference between the first and second supply voltages +Ub and −Ub is applied to each amplifier wing 12A, 12B. The amplifier stage 12 can therefore operate with half the supply voltage of a conventional Class AB power amplifier or provide double the output voltage with the same supply voltages.

The power transistors T, T' are configured in such a way that the voltages across the emitter resistor R7, R7', which act as current sensing resistors, follow the input voltage. Consequently the current through the respective first or second winding 13A, 13B of the coupling transformer 13 follows the input signal. If the input voltage varies, this arrangement will act as a voltage-to-current converter (voltage-controlled current source VCCS).

Since the current is maintained practically independently of the load and therefore of the length of the connecting line between the collector of the power transistors T, T' and the coupling transformer 13, the amplifier stage 12 and the coupling transformer 13 can be arranged in different housings and can be connected by a transmitter cable TC having a length, e.g. of a few meters, which allows placing the modules of the metal detection apparatus in different locations as required by a production process.

FIG. 2 further shows that reference signals R, R' are taken from the collectors of the power transistors T, T' and routed to reference inputs of the signal processing unit 4, particularly the signal processor 42. With phase detectors implemented in the signal processing unit 4 or signal processor 42, the response signals can be demodulated in order to detect signals relating individually to contaminants or products. Secondary windings in the coupling transformer 13, as used in the system of FIG. 1, are avoided.

In this preferred embodiment of the invention the first and second windings 13A, 13B are primary windings of the coupling transformer 13 and the third winding 13C is a secondary winding of the coupling transformer 13.

The third winding 13C of the coupling transformer 13 comprises a plurality of tappings 150, 151, 152, 153, 154. The first end of the transmitter coil 21 is fixedly connected to the tapping 150 and wherein the second end of the transmitter coil 21 is selectively connectable via a third switch 15 to one of the other tappings 151, 152, 153, 154 of the third winding 13C of the coupling transformer 13. By using primary windings 13A, 13B and a secondary winding 13C the ratio of the inductance of the first and second windings 13A, 13B, 13C of the transformer 13 and the reflected inductance of the transmitter coil 21 is finely selectable in a wider range of tap combinations compared to the system of FIG. 1 to provide an optimum impedance match between the amplifier to the transmitter coil 21.

In the embodiment shown in FIG. 2 the first end of the transmitter coil 21 is connectable via a fourth switch 23 to one of three tuning capacitors 221, 222, 223, which are connected directly or via a part, e.g. a plurality of turns, of the third winding 13C of the coupling transformer 13 and the third switch 15 to the second end of the transmitter coil 21.

Hence, the transmitter coil 21 and the connected tuning capacitors 221, 222, 223 form a resonant circuit that can optimally be tuned. By connecting at least one of the tuning capacitors 223 via a number of turns of the third winding 13C of the coupling transformer 13 to the transmitter coil 21 the resulting resonant circuit can be tuned to lower frequencies so that the resonant circuit can resonate as frequencies in the range of 25 kHz to 850 kHz.

The control unit 5, for example a processor or personal computer, communicates with the signal processing unit 4 via a bus system 60. Hence, the control unit 5 can provide operating parameters to the signal processing unit 4, particularly to the signal processor 42, and collect measurement data gained in the signal processing unit 4, which can also be integrated in the control unit 5. Further, the control unit 5 provides control signals via control lines or control buses 51, 52A, 52B, 53 and 54 to the frequency generator 11 for selecting an operating frequency, to the first and second switch or switch bank 14A, 14B for selectively connecting the amplifier stage 12 to the primary windings 13A, 13B of the transformer 13, to the third switch or switch bank 15 for selectively connecting the transmitter coil 21 to the secondary winding 13C of the transformer 13 and to the fourth switch or switch bank 23 for selectively connecting one or more of the tuning capacitors 221, 222, 223 to the transmitter coil 21.

What is claimed is:
1. An apparatus for detecting metal, comprising:
 a transformer unit, comprising:
  a frequency generator;
  an amplifier stage that receives an input signal $S_{IN}$ having a selectable operating frequency from the frequency generator, the amplifier stage comprising a first amplification wing and a second amplification wing, each amplification wing having a power transistor, the first amplification wing arranged to amplify a first half wave of the input signal and the second amplification wing arranged to amplify a second half wave of the input signal; and a coupling transformer, comprising:
a first winding and a second winding, each of which is connected, at a first end, to a supply voltage ($+U_b$) and, at one of at least one tappings, at a same turn number counted from the first end of the first winding and the second winding, the first winding is connected to the power transistor of the first amplification wing and the second winding is connected to the power transistor of the second amplification wing; and
a third winding;

a transmitter unit comprising a transmitter coil that is connected to the third winding;

a receiver coil set, where each of a first and a second receiver coil is coupled to the transmitter coil; and a signal processing unit, where a receiver unit receives input from the respective receiver coils and passes a signal to a signal processor.

2. The apparatus of claim 1, further comprising:
a first switch, through which the first power transistor is connectable to one of the first tappings; and
a second switch, through which the second power transistor is connectable to one of the second tappings;
wherein the first and second windings each have an identical number of turns, with the respective first and second tappings connected to identical turn numbers of the first and the second winding.

3. The apparatus of claim 2, wherein:
each of the first and second power transistors has a collector that is connectable to one of the respective first and second tappings through the respective first and second switch;
the first end of each of the windings, which are wound in an inverse sense relative to each other, is connected to a first supply voltage (+Ub).

4. The apparatus of claim 3, wherein:
the collector of the first power transistor is connected to the first supply voltage (+Ub) via the first winding;
the emitter of the first power transistor is connected to a second supply voltage (−Ub) via a first emitter resistor;
the collector of the second power transistor is connected to the first supply voltage (+Ub) via the second winding;
the emitter of the second power transistor is connected to the second supply voltage (−Ub) via a second emitter resistor; and
the base of each of the first and the second power transistor is provided with corresponding resistor networks having identical bias voltages.

5. The apparatus of claim 3, wherein:
the first amplification wing further comprises a first amplification unit with an inverting and a non-inverting input and an output connected to the base of the first power transistor;
the second amplification wing further comprises a second amplification unit with an inverting and an non-inverting input and an output connected to the base of the first power transistor;

the noninverting input of the first amplification unit is connected to the inverting input of the second amplification unit; and
the frequency generator applies the input signal ($s_{IN}$) to the inverting input of the first amplification unit and to the noninverting input to the second amplification unit, so that the input signal ($s_{IN}$) is inverted in the second amplification unit.

6. The apparatus of claim 5, wherein:
a voltage potential, corresponding to one-half of the second supply voltage (−Ub), is connected to the noninverting input of the first amplification unit via a first resistor and to the inverting input of the second amplification unit via a second resistor.

7. The apparatus of claim 6, further comprising:
one or more tuning capacitors, such that the first end of the transmitter coil is selectively connectable via a switch to one side of the one or more tuning capacitors and the other side of the one or more tuning capacitors is connected to the second end of the transmitter coil, either directly or via a part of the third winding.

8. The apparatus of claim 6, wherein:
the frequency generator allows the selection of two or more operating frequencies ($f_{TX}$), preferably in the range of 25 kHz to 850 kHz.

9. The apparatus of claim 6, wherein:
at the lowest operating frequency provided, the ratio of the reflected inductance of the first and second windings is selectable with at least 50 tap combinations, to provide an optimum impedance match between the amplifier and the transmitter coil.

10. The apparatus of claim 6, wherein:
each of the power transistors is an NPN transistor.

11. The apparatus of claim 3, wherein:
reference inputs of the signal processing unit are provided by the respective collectors of the first and the second power transistor or the selected first and second tappings.

12. The apparatus of claim 1, wherein:
the amplifier stage is arranged in a first housing;
the coupling transformer is arranged in a second housing; and
a transmitter cable connects the collectors of the respective first and second power transistors to the corresponding first and second switch.

13. The apparatus of claim 1, wherein:
the coupling transformer has the first and second windings as primary windings and the third winding as a secondary winding.

14. The apparatus of claim 1, wherein:
the third winding of the coupling transformer comprises a plurality of tappings, one of which is connected to the first end of the transmitter coil, and a third switch, which selectively connects another one of the plurality of tappings to the second end of the transmitter coil.

15. The apparatus of claim 1, further comprising:
one or more tuning capacitors, such that the first end of the transmitter coil is selectively connectable via a switch to one side of the one or more tuning capacitors and the other side of the one or more tuning capacitors is connected to the second end of the transmitter coil, either directly or via a part of the third winding.

16. The apparatus of claim 1, wherein:
the frequency generator allows the selection of two or more operating frequencies ($f_{TX}$), preferably in the range of 25 kHz to 850 kHz.

17. The apparatus of claim 1, wherein:
at the lowest operating frequency provided, the ratio of the reflected inductance of the first and second windings is selectable with at least 50 tap combinations, to provide an optimum impedance match between the amplifier and the transmitter coil.

18. The apparatus of claim 1, wherein:
each of the power transistors is an NPN transistor.

\* \* \* \* \*